United States Patent

Ma et al.

[11] Patent Number: 5,857,973
[45] Date of Patent: Jan. 12, 1999

[54] FUZZY LOGIC TISSUE FLOW DETERMINATION SYSTEM

[75] Inventors: Qinglin Ma, Bothell; John C. Lazenby, Fall City, both of Wash.

[73] Assignee: Siemens Medical Systems, Inc., Iselin, N.J.

[21] Appl. No.: 938,480

[22] Filed: Sep. 30, 1997

[51] Int. Cl.$^6$ .................................................... A61B 8/06
[52] U.S. Cl. ......................................... 600/441; 600/454
[58] Field of Search ................................. 600/454, 455, 600/441

[56] References Cited

U.S. PATENT DOCUMENTS

| | | | |
|---|---|---|---|
| 537,965 | 10/1895 | Hall et al. | |
| 4,794,932 | 1/1989 | Baba | 600/455 |
| 5,042,491 | 8/1991 | Amemiya | 600/455 |
| 5,190,044 | 3/1993 | Kawasaki et al. | 600/455 |
| 5,279,302 | 1/1994 | Tamano et al. | 600/455 |
| 5,357,965 | 10/1994 | Hall et al. | 600/454 |
| 5,462,059 | 10/1995 | Ferrara et al. | 600/455 |
| 5,487,389 | 1/1996 | Bonjanin et al. | 600/455 |
| 5,513,640 | 5/1996 | Yamazaki et al. | 600/455 |
| 5,515,852 | 5/1996 | Karp et al. | 600/455 |
| 5,623,929 | 4/1997 | Weng | 600/455 |

*Primary Examiner*—Francis J. Jaworski

[57] ABSTRACT

A fuzzy logic tissue/flow determination system receives echo amplitude, color amplitude, and velocity signals from an ultrasound imaging system. These values are applied to a set of fuzzy rules which quantify the amount by which the signal values vary from preset thresholds. The outputs of the fuzzy rules provide an indication of the plausibility that the echo signals represent a tissue or flow condition. The outputs from all the fuzzy rules are combined and de-fuzzified to produce a combined plausibility of the signals representing either a tissue or flow condition. The tissue/flow decision is made based on which plausibility is larger.

6 Claims, 5 Drawing Sheets

FUZZY LOGIC TISSUE FLOW DETERMINATION SYSTEM

FIELD OF THE INVENTION

The present invention relates to ultrasound systems, and in particular to systems for determining tissue/flow conditions for display in an ultrasound image.

BACKGROUND OF THE INVENTION

Ultrasound is a medical imaging technique whereby high frequency acoustic signals are applied to a body. The magnitude and frequency shift of the echo signals that are created are detected and used to create images of the internal body matter of a patient.

Most high-end ultrasound imaging machines operate in at least two distinct modes. When operating in a brightness or B-mode, the ultrasound system produces a greyscale image of the internal body matter, such as bones, muscles, organs, etc., of a patient. When operating in a color mode, the ultrasound system produces a composite image where the non-moving body matter is shown in greyscale and moving body matter, such as blood flow is shown in color over the greyscale image.

In the color mode, the ultrasound system must determine whether the echo signals received from a patient are indicative of blood flow or non-moving tissue. In particular, the ultrasound system must distinguish between real blood flow signals and those signals that appear to be caused by blood flow but are in fact caused by tissue motion, vessel wall motion due to breathing, heart induced motion, ultrasound probe movement, etc.

The traditional approach used to make a tissue/flow decision is to compare the magnitude and velocity of the received echo signals against some predetermined thresholds. Those signals with values less than the thresholds are deemed to be tissue and are displayed in greyscale. Those signals with values greater than the thresholds are assumed to be blood flow and are displayed in color. While this method works well for distinguishing echo signals that are clearly above and below the thresholds, the crisp threshold approach does not work well where echo signals are received from slow moving blood or from vessel walls. As a result, many conventional ultrasound imaging systems cannot actually produce images of slow moving blood.

Given the shortcomings in conventional color flow imaging systems, there is a need for a tissue/flow determination system that has an enhanced ability to detect slow moving blood flow in areas of moving tissue.

SUMMARY OF THE INVENTION

To compensate for problems associated with prior art, crisp tissue/flow determination systems, the present invention comprises a fuzzy logic tissue/flow determination system. Raw echo amplitude, color amplitude, and velocity values are supplied as input to a set of fuzzy rules that evaluate an echo plausibility and color plausibility function to produce an indication of the possibility that the echo signals represent either tissue or blood flow. The echo color probabilities from each of the fuzzy rules are aggregated and "de-fuzzified" to produce an indication of the plausibilities that the echo signals represent tissue or blood flow. The determination of whether to show the echo signals as tissue or blood flow is based on which possibility is larger.

In a preferred embodiment of the invention, a look up table stores a color amplitude threshold value that is selected for a particular combination of echo amplitude and velocity signal values such that if the color amplitude signal received exceeds the color amplitude threshold, then the signals are shown as flow. Otherwise, the signals are shown as tissue.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

The present invention is a fuzzy logic tissue/flow determination system that has an increased ability to distinguish slow moving blood flow from slowly moving tissue for display in an ultrasound image.

Figure 1:
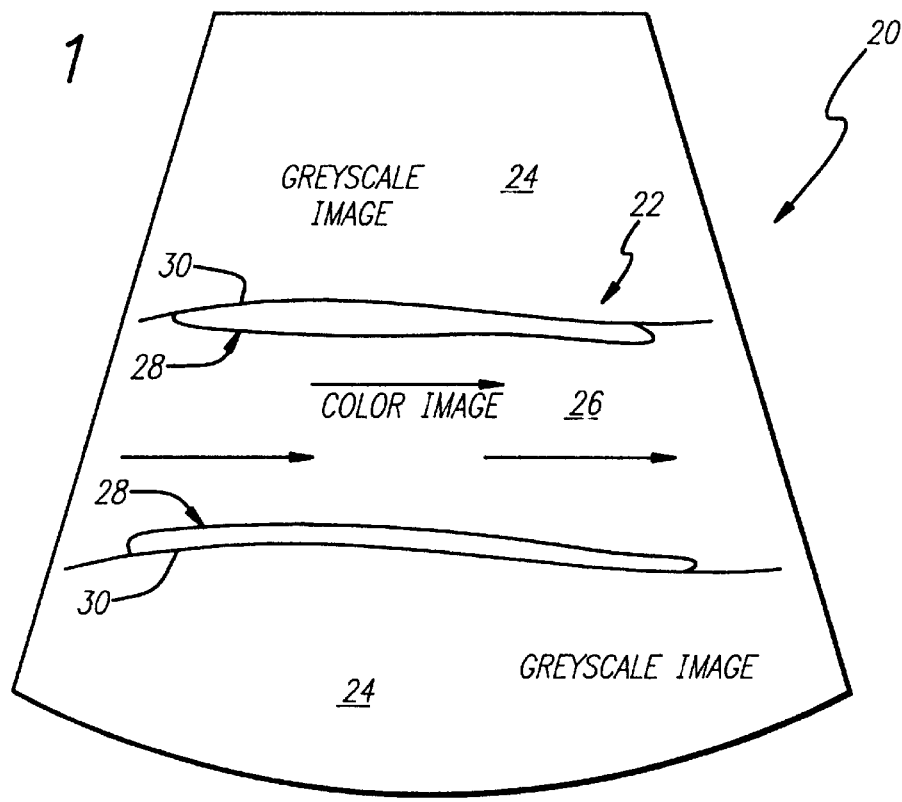
FIG. 1 illustrates a typical color flow ultrasound image.

FIG. 1 illustrates a typical color flow ultrasound image 20. The image shows a blood vessel 22 within a layer of tissue 24. Because the tissue is not moving or is moving only slowly, it is shown in greyscale. Within the blood vessel is a stream of moving blood 26 that is shown in colors that are dependent on the velocity of the blood flow. Typically, the blood flow exhibits a velocity profile that is faster at the center of the vessel and slows to zero velocity at the vessel walls. In conventional color flow ultrasound imaging systems, it is difficult to distinguish the slow moving blood that is found in an area 28 near a wall 30 of the vessel and the vessel wall itself. Therefore, the areas 28 are often shown as greyscale tissue rather than slowly moving blood flow. Because many diseases are diagnosed by the characteristics of blood flow near a vessel wall, it is important to be able to better identify slowly moving blood.

In conventional ultrasound imaging systems, the tissue/flow determination is made on the basis of one or more thresholds against which the echo signals received by the ultrasound system are compared. If the color amplitude and velocity are greater than the thresholds, then the echo signals are shown in color. Otherwise, the signals are shown in greyscale. However, the binary nature of a threshold comparison is inadequate to clearly distinguish slowly moving blood flow from tissue walls and is susceptible to producing artifacts that occur as a result of the cardiac cycle, breathing, or probe movement.

In fuzzy logic, the crisp decisions that were made by comparing echo signals with predefined thresholds are replaced with fuzzy logic statements that quantify the extent to which the echo signals are indicative of a tissue/flow condition and to make a final decision based on which condition is more plausible.

Figure 2:
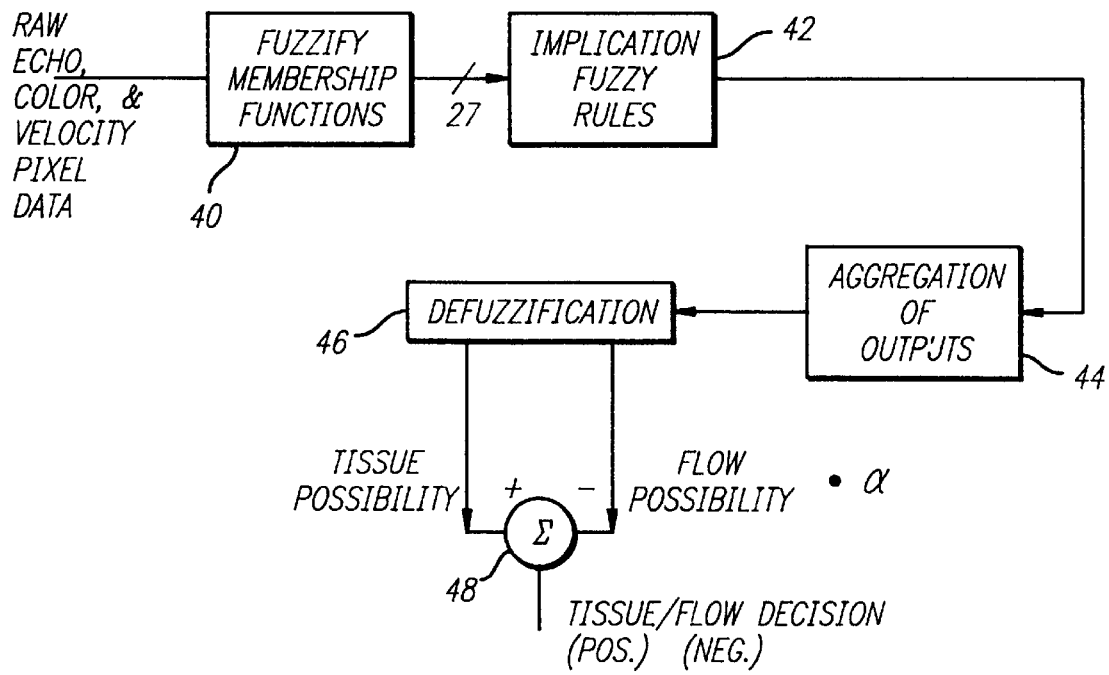
FIG. 2 is a block diagram of a fuzzy logic tissue/flow determination system according to the present invention.

FIG. 2 illustrates a block diagram of the fuzzy logic tissue/flow determination system according to the present invention. Raw echo amplitude E, color amplitude C and velocity V signals are preferably received from a beamformer of the ultrasound system and applied to a set of membership functions 40 that quantify the extent to which the signals are smaller than, around, or larger than a set of thresholds used to detect blood flow. The velocity signal is defined by:

$$V = \tan\left(\frac{N}{D}\right) \quad \text{Eq. 1}$$

and the color amplitude signal is defined as:

$$C = \sqrt{N^2 + D^2} \quad \text{Eq. 2}$$

where D and N are the real and imaginary parts of the first-lag of the autocorrelation function R1. Similarly, if the fuzzy logic tissue/flow determination system of the present invention is to be used for power mode or color amplitude mode, then the zero-lag autocorrelation of the echo signals can be used.

Because there are three membership functions (smaller than, around, and larger than) that are evaluated for each of the echo amplitude, color amplitude and velocity signals, there are twenty-seven possible combinations that are applied as inputs to a set of fuzzy rules 42. The fuzzy rules provide an indication of the likelihood of a set of echo signals being representative of tissue or moving blood flow. The outputs from each of the fuzzy rules 42 are aggregated by selecting the maximum at a block 44. The outputs are then "de-fuzzified" at a block 46 in order to produce a numerical indication of the possibility that a set of echo signal represents tissue or moving blood flow. The possibility that a set of echo signals is representative of tissue is applied to a positive input of a differencing circuit 48, while the possibility that the echo signals is representative of blood flow is applied to a negative input of the differencing circuit. The differencing circuit subtracts two input values to determine which condition is more probable. If the result is positive, the echo signals are shown in the ultrasound image as tissue. Alternatively, if the output of the differencing circuit 48 is negative, then the echo signals are shown in the image as blood flow. If desired, the flow plausibility that is applied to the differencing circuit 48 can be weighted by a factor a that is slightly less than one, e.g., 0.95, so that in ambiguous situations, the echo signals will more likely be shown as tissue rather than blood flow.

Figure 3A:
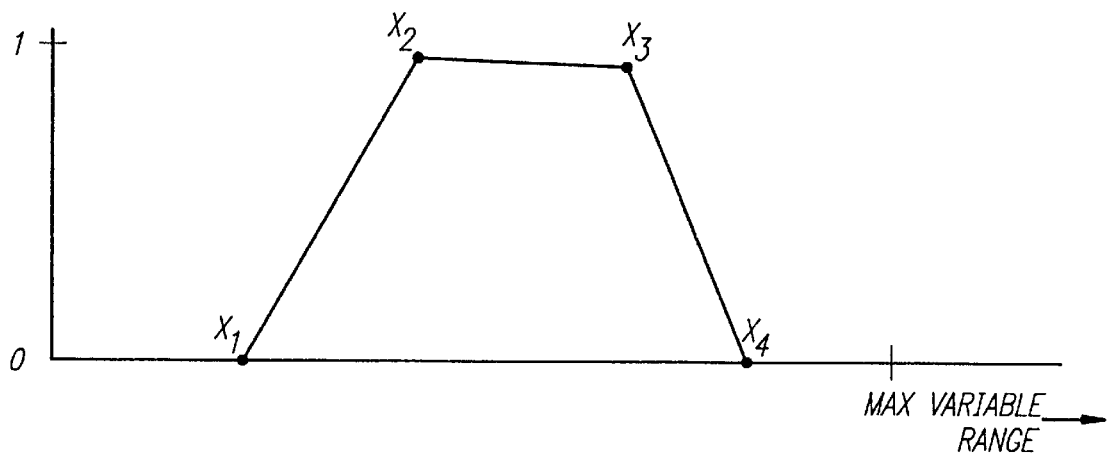
FIGS. 3A and 3B illustrate generic membership, echo plausibility, and color plausibility functions used by the fuzzy logic tissue/flow determination system of the present invention.

FIG. 3A illustrates a generic form of a membership function used by the present invention to determine whether the echo amplitude, color amplitude, and velocity signals received from the ultrasound system are representative of tissue or blood flow. Each membership function can be defined by four points (X1, X2, X3, X4), where X1 is the start point, X4 is the stop point, and the points X2 and X3 define the shoulders of the membership function.

When plotted on a two-dimensional graph, the points in the membership function can have a vertical component that ranges between zero, meaning the point in question is absolutely false, to one, meaning the point in question is absolutely true. On the horizontal axis, the points in the membership function can have any valid signal that is returned by the ultrasound machine.

The starting point X1 and ending point X4 of the membership function have a vertical component of zero, while the shoulder points X2 and X3 have vertical components of 1. Any adjacent points may have the same horizontal component value to change the shape of the membership function.

The following table defines the horizontal components of the points X1, X2, X3, and X4 of presently preferred membership functions for determining tissue/flow conditions with echo signals received from a Siemens' Sonoline® Elegra ultrasound, machine. As will be appreciated from the table, the membership functions set an echo amplitude threshold equal to 1600, a color amplitude threshold equal to 50 and a velocity threshold equal to 25. However, these thresholds are typically specific to the flow conditions in the body from which the echo signals are obtained. These flow conditions may include the vessel location and size. Such thresholds may be selected by the user for the particular type of tissue being examined.

TABLE 1

Parameters for the Membership Functions

| Fuzzy Variable | Variable Range | Linguistic Description | (X1, X2, X3, X4) |
|---|---|---|---|
| Echo Amplitude | 0 to 4000 | smaller than | (0, 0, 1570, 1600) |
| | | around | (1570, 1600, 1600, 1630) |
| | | larger than | (1600, 1630, 4000, 4000) |
| Color Amplitude | 0 to 3000 | smaller than | (0, 0, 0, 50) |
| | | around | (0, 50, 50, 100) |
| | | larger than | (50, 100, 3000, 3000) |
| Velocity | 0 to 250 | smaller than | (0, 0, 10, 25) |
| | | around | (10, 25, 25, 40) |
| | | larger than | (25, 40, 250, 250) |

Figure 3B:
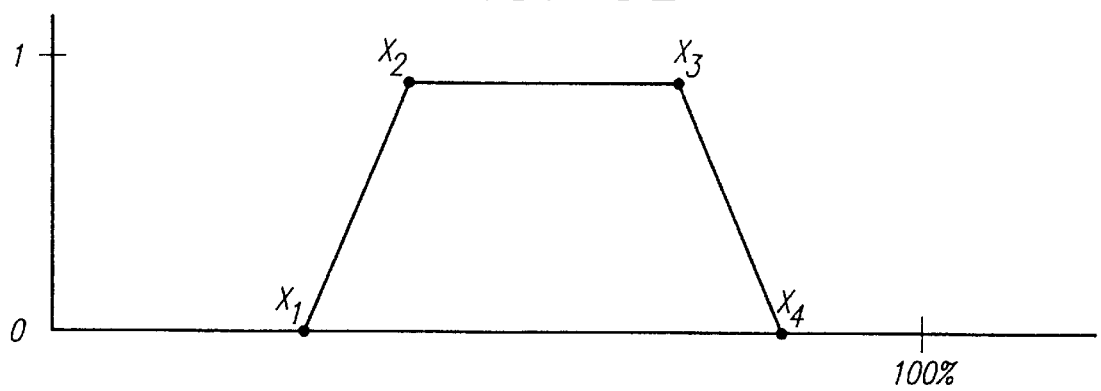

FIG. 3B illustrates a generic form of a plausibility function that provides a possibility that the set of echo signals represent tissue or blood flow. Again, each plausibility function can be defined by four points (X1, X2, X3, X4). When plotted on a two-dimensional graph the points in the plausibility function can have a vertical component that varies between zero, representing absolutely false, and one, representing absolutely true. On the horizontal axis, the points in the plausibility function can have values between 0 percent possibility and 100 percent possibility. Again, the start point XI and the stop point X4 have vertical components equal to zero, while the two shoulder points X2 and X3 have vertical components equal to 1.

In the presently preferred embodiment of the invention, it has been determined that five membership functions are needed to define the possibility that a set of echo signals is representative of a tissue or flow condition. These functions include a low, low-medium, medium, upper-medium, and high plausibility membership functions for both echo plausibility and color plausibility. The horizontal components for each of the points X1, X2, X3, and X4 in the echo plausibility and color plausibility function are defined as follows.

TABLE 2

Parameters for the Membership Functions

| Fuzzy Variable | Variable Range | Linguistic Description | (X1, X2, X3, X4) |
|---|---|---|---|
| Echo Plausibility | 0 to 100 | small | (0, 0, 0, 25) |
| | | Lmedium | (0, 25, 25, 50) |
| | | medium | (25, 50, 50, 75) |
| | | Umedium | (50, 75, 75, 100) |
| | | high | (50, 75, 100, 100) |
| Color | 0 to 100 | small | (0, 0, 0, 25) |

TABLE 2-continued

Parameters for the Membership Functions

| Fuzzy Variable | Variable Range | Linguistic Description | (X1, X2, X3, X4) |
|---|---|---|---|
| Plausibility | | Lmedium | (0, 25, 25, 50) |
| | | medium | (25, 50, 50, 75) |
| | | Umedium | (50, 75, 75, 100) |
| | | high | (75, 100, 100, 100) |

As indicated above, there are three membership functions that are evaluated for each of the echo amplitude, color amplitude, and velocity values obtained from the ultrasound system. These three membership functions provide twenty-seven different permutations of functions that are evaluated to determine whether it is more likely that the signals represent tissue or moving blood flow. The following table defines each combination of membership functions that are evaluated against one of the five echo plausibility and color plausibility functions. For example, rule #1 specifies that "if the echo amplitude is smaller than its threshold Et, and the color amplitude is smaller than its threshold Ct, and the velocity is smaller than its threshold Vt, then the plausibility of an echo is in the small range and the plausibility of having to display the signals in color is small."

TABLE 3

Fuzzy Rules

| Rule # | Echo Amplitude | Color Amplitude | Velocity | Echo Plausibility | Color Plausibility |
|---|---|---|---|---|---|
| 1 | small | small | small | small | small |
| 2 | small | small | around | small | small |
| 3 | small | small | larger | small | Lmedium |
| 4 | small | around | small | small | small |
| 5 | small | around | around | small | Lmedium |
| 6 | small | around | larger | small | medium |
| 7 | small | larger | small | small | small |
| 8 | small | larger | around | small | Umedium |
| 9 | small | larger | larger | small | high |
| 10 | around | small | small | Lmedium | small |
| 11 | around | small | around | small | Lmedium |
| 12 | around | small | larger | small | medium |
| 13 | around | around | small | Lmedium | small |
| 14 | around | around | around | Lmedium | Lmedium |
| 15 | around | around | large | small | Umedium |
| 16 | around | large | small | Lmedium | small |
| 17 | around | large | around | Lmedium | medium |
| 18 | around | large | large | small | Umedium |
| 19 | large | small | small | high | small |
| 20 | large | small | around | high | small |
| 21 | large | small | large | Umedium | Lmedium |
| 22 | large | around | small | high | small |
| 23 | large | around | around | medium | Lmedium |
| 24 | large | around | large | Lmedium | Umedium |
| 25 | large | large | small | Umedium | small |
| 26 | large | large | around | medium | Lmedium |
| 27 | large | large | large | high | Umedium |

For a set of echo amplitude, color amplitude, and velocity signals, each of the twenty-seven rules is evaluated and compared to the echo plausibility and color plausibility tables as specified by the twenty-seven fuzzy rules. The outputs of the twenty-seven fuzzy rules are aggregated by selecting the maximum to obtain a combined echo and color plausibility function. The combined functions are then "de-fuzzified" by determining center of mass of each combined plausibility function in order to determine which state, i.e., tissue or flow, is more probable. The ultrasound signals are then displayed in greyscale if the samples most likely represent tissue, or in color if the samples most likely represent moving blood flow.

Figure 4:
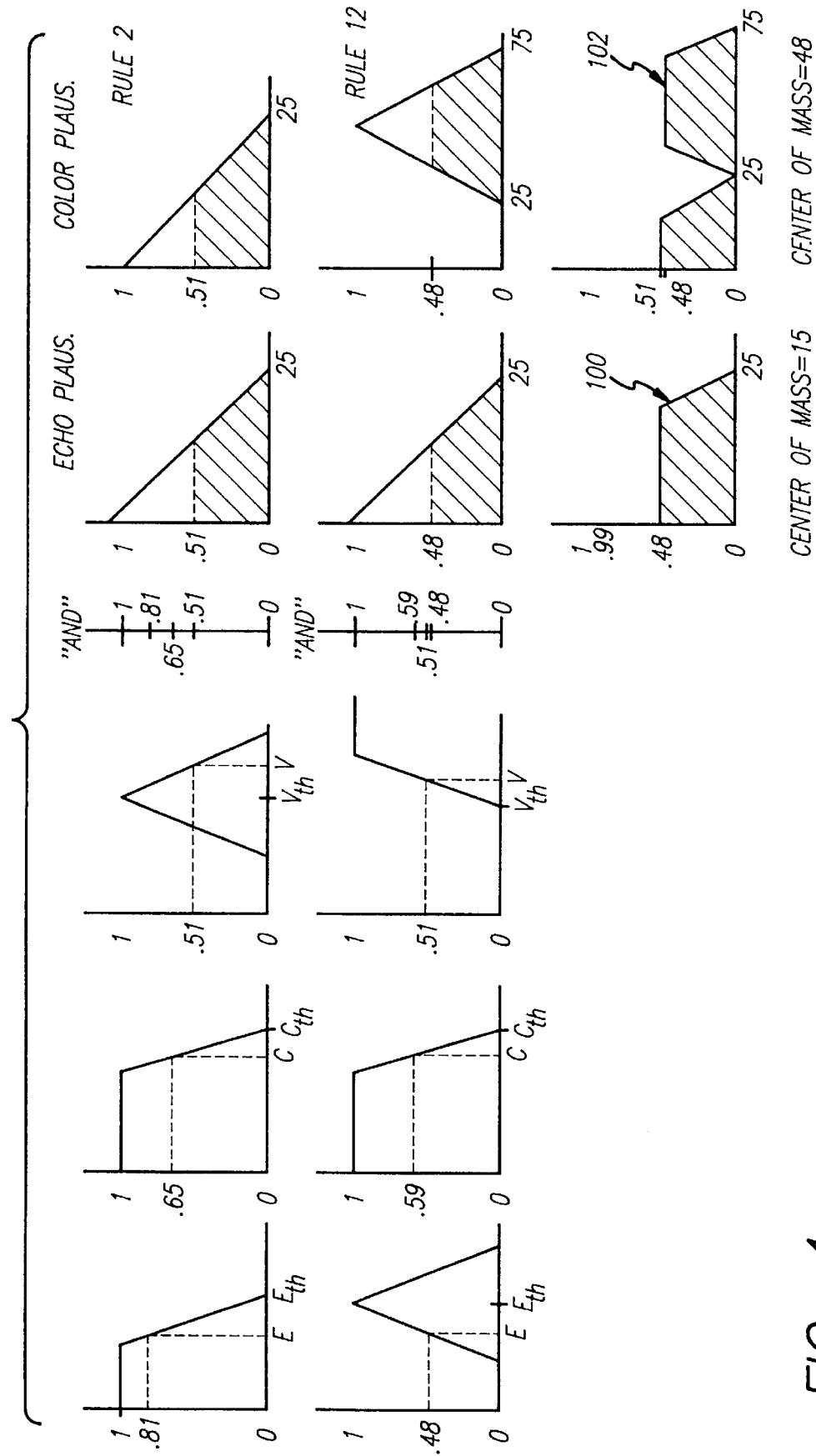
FIG. 4 illustrates the application of two fuzzy rules used by the present invention to make a tissue/flow determination.

FIG. 4 illustrates the operation of the tissue/flow determination system according to the present invention using two of the twenty-seven rules. In particular, rule #2 and rule #12 are shown. As can be seen from Table 3, rule #2 specifies that the echo amplitude is compared to the "smaller than" echo amplitude membership function, the color amplitude is compared to the "smaller than" membership function, and the velocity is compared to the "around" membership function. The results of these comparisons are compared to the "small" echo plausibility function and the "small" color plausibility function. Similarly, rule #12 specifies that the echo amplitude is compared to the "around" membership function, the color amplitude is compared to the "small" membership function and the velocity is compared to the "larger" membership function. The results of the these comparisons are compared to the small echo plausibility function and to the "medium" color plausibility function.

As shown in FIG. 4, the echo amplitude E, color amplitude C, and velocity V values received from the ultrasound system for the point in question are compared to the membership functions specified by the rule. Each comparison provides a numeric indication of how much the value is smaller than, around, or larger than the corresponding echo amplitude, color amplitude, and velocity threshold. In the example shown, the "smaller than" echo amplitude function returns a value of 0.81. The "smaller than" color amplitude function returns a value of 0.65 and the "around" threshold velocity membership function returns a value of 0.51. The values produced by the membership functions are ANDed together which has the effect of selecting the smallest value produced. The smallest value 0.51, is mapped onto the echo plausibility and color plausibility function to define an area for these functions as indicated by the dashed lines.

In rule #12, the same echo amplitude E, color amplitude C, and velocity V values are compared against the membership functions specified. In this case, the "around" echo threshold returns a value of 0.48, the "smaller than" color threshold membership function returns a value of 0.59, and the "larger than" velocity threshold membership function returns a value of 0.51. Again, these values are ANDED together to select the smallest one, namely 0.48. This value is mapped onto the echo plausibility and color plausibility function specified to define an area indicated by the hash lines.

After each of the fuzzy rules has been evaluated for a set of echo signals, the areas specified by the echo plausibility and color plausibility functions are aggregated by selecting the maximum to produce a combined echo plausibility function 100 that is the result of taking the maximum of the echo plausibility functions produced for rule #2 and rule #12. Similarly, a combined color plausibility function 102 is the result of taking the maximum of the color plausibility functions evaluated for rule #2 and rule #12.

Once the aggregated echo plausibility functions and color plausibility functions have been calculated, these plausibility functions are "de-fuzzified" to produce a numerical indication of which condition is more likely. In the presently preferred embodiment of the invention, the plausibility functions are "de-fuzzified" by calculating a center of mass of each of the combined functions. For example, the center of mass of the combined echo plausibility function 100 may be 9.7, while the center of mass of the combined color plausibility function 102 may be 36.6. That is to say, the likelihood that the echo, color, and velocity signals represent tissue is 9.7 percent while the likelihood that they represent moving blood flow is 36.6 percent. Because the likelihood indicated by the center of mass of the combined color plausibility function is greater than the likelihood indicated by the combined echo plausibility function, the echo signals are shown in color in the corresponding ultrasound image.

As will be appreciated, the example shown in FIG. 4 is only shown for two of the twenty-seven rules. In an actual embodiment of the invention, the same calculations are performed using all twenty-seven fuzzy rules.

In some instances, it may be too time consuming or require too much processing power to compute the results for all twenty-seven fuzzy rules. In that case, the number of rules can be reduced. For example, rules #1–#9 all produce a small echo plausibility. Therefore, these rules can be combined into a single rule that states "if the echo amplitude is smaller than the echo amplitude threshold, then the echo plausibility is small."

Figure 5:
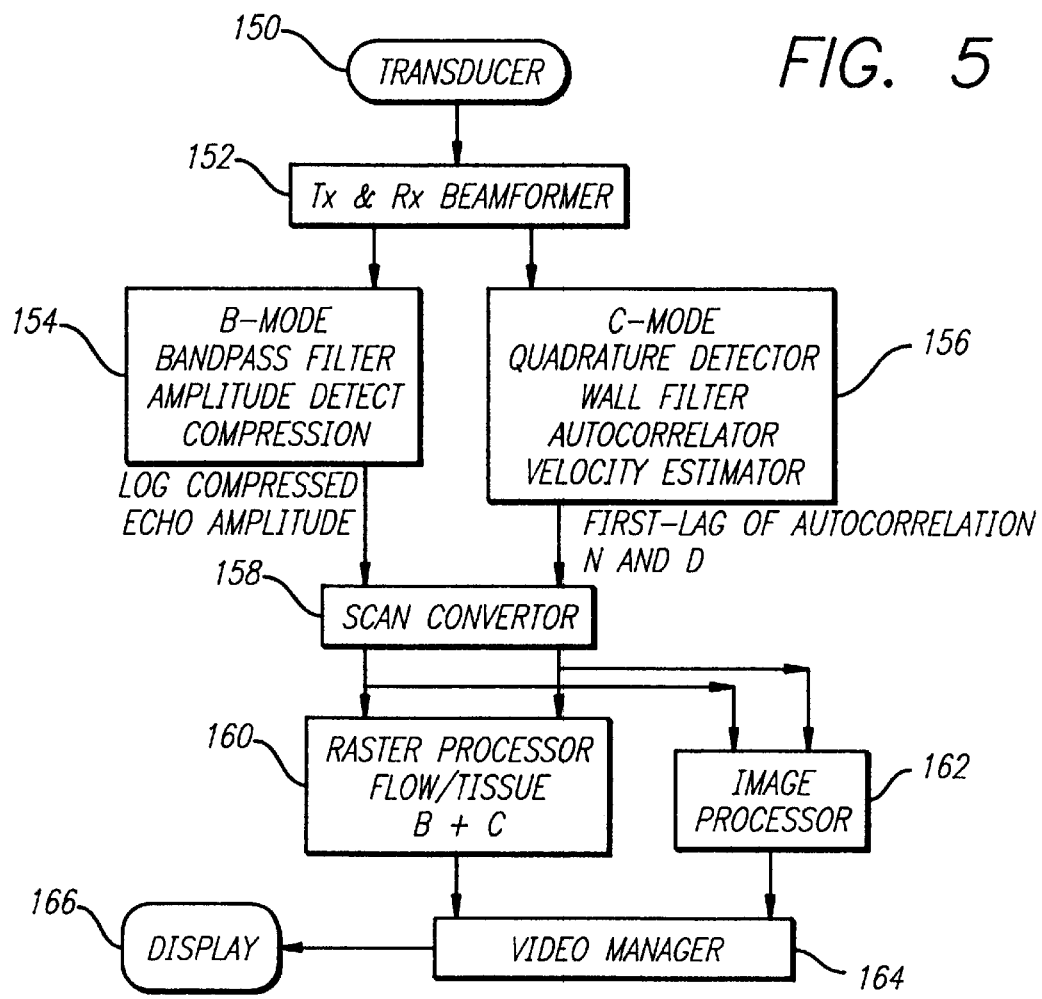
FIG. 5 is a block diagram of an ultrasound system in which the fuzzy logic tissue/flow determination system according to the present invention is implemented.

FIG. 5 is a block diagram of an ultrasound system in which the fuzzy logic tissue/flow determination system according to the present invention is implemented.

A transducer 150 supplies the ultrasonic signals to the patient and detects the returned echo signals. Controlling the timing at which the ultrasonic signals are transmitted from the transducer 150 and the time at which the returned echo signals are combined in a beamformer 152. The combined echo signals produced by the beamformer 152 are fed as inputs to a B-mode processor 154 and a color mode processor 156. The B-mode processor 154 filters out the unwanted frequency components, determines the amplitude of the received echo signals, and compresses the echo amplitude signals to reduce the dynamic range of the amplitude signals for further processing.

The color mode processor 156 divides the received echo signals into their in-phase and quadrature components, applies a wall filter to reduce the effect of echo signals produced by moving vessel walls, calculates the zeroth and first-lag autocorrelation functions, and estimates the velocity.

The outputs of the B-mode processor 154 and color mode processor 156 are fed into a scan converter 158 that converts the geometry of the signals produced by the transducer into a form that can be shown on a video display. The output of the scan converter 158 is fed into a raster processor 160, which combines the B-mode and color mode image into a single combined image.

The tissue/flow decision can be made using either pre- or post-scan converted data. If pre-scan converted data are used, it is possible to route pre-wall filtered color amplitude data into the B-mode processing chain so that the data for the B and color modes have the same beamlines and axial samples.

In the Elegra ultrasound machine, the raster processor preferably makes the tissue/flow decision that determines whether the pixels in the image will be displayed in greyscale, or color. An alternative is to use an image processor 162. It can replace the function of both scan converter and raster processor or raster processor only. The outputs of the raster processor 160 or the image processor 162 are fed into a video manager 164 that converts the signals to the appropriate video levels that are supplied to a video display 166 in order to produce the ultrasound image.

An efficient implementation of the fry logic tissue/flow determination system of the present invention can be made by observing that the tissue flow decision is monotonic in color amplitude. That is to say, if the algorithm concludes that for a given triplet of input values (echo amplitude, color amplitude, and velocity) that the output should be flow, then the output will also be flow for all greater values of color amplitude. Therefore, for every pair of echo amplitude and velocity values, there is a color amplitude threshold for which color amplitude values greater than the threshold should be displayed as flow and for color amplitude values less than the threshold should be displayed as tissue. Therefore, a table of threshold values can be constructed that is indexed by echo amplitude and velocity.

Because in the present embodiment of the invention, the echo amplitude can range over 4,000 possible values and the velocity can range over 250 possible values, the threshold would need 4,000*250=1,000,000 entries. To reduce the size of the color amplitude threshold table, it is recognized that the echo amplitude membership functions only change in the range of 1,570–1,630. Similarly, the velocity membership functions only change in the range of 10–40, and the color amplitude membership functions only change in the range 0–100. Considering the echo amplitude, only one table index is needed for all values less than or equal to 1,570 because the membership functions take on the same value for that entire range of inputs. Similarly, the membership functions do not vary for echo amplitude values of 1,630 or greater. Consequently, the threshold table really only need contain 61*31=1,891 entries.

Figure 6:
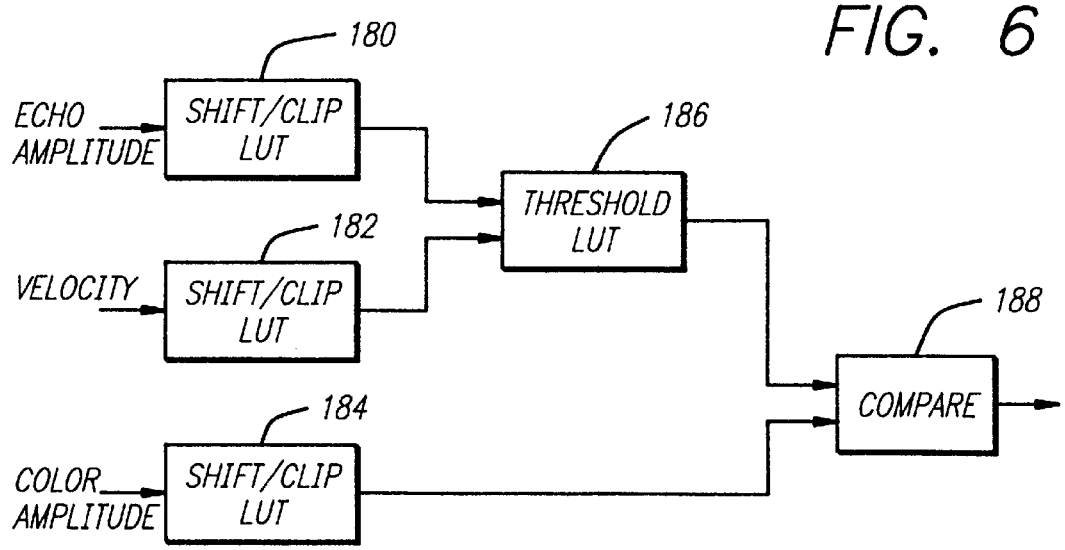
FIG. 6 is a block diagram of a number of look up tables that can implement the fuzzy logic tissue/flow determination system of the present invention.

FIG. 6 illustrates an efficient implementation of the tissue/flow determination system of the present invention. The determination system includes three look up tables 180, 182, and 184. The look up table 180 receives the echo amplitude signal and subtracts 1,570 from the input value and clips the result to the range 0–60. The look up table 182 receives the velocity value and subtracts 10 from the input value and clips the result to the range 0–30. The look up table 184 receives the color amplitude signals as an input value, and simply clips the input to the range 0–100. The outputs of the look up tables 180 and 182 are supplied as inputs to a color amplitude threshold look up table 186. The table 186 produces a color amplitude threshold above which any value of color amplitude indicates flow and below which indicates tissue. The threshold value retrieved from the look up table 186 is applied as an input to a comparator 188 that compares the threshold value with the clipped color amplitude value produced by the look up table 184. If the color amplitude value is greater than the threshold value, then the output of the comparator 188 indicates that the corresponding pixels in a display should be shown as color flow. Alternatively, if the output of the look up table 184 is less than the threshold value produced by the look up table 186, then the comparator 188 produces an indication that the pixels should be displayed as tissue.

The values stored in the look up table 186 are preferably determined off line using a commercially available fuzzy logic inference engine that performs the fuzzy logic calculations described above for all possible combinations of echo amplitude, color amplitude, and velocity values. One example of a fuzzy logic inference engine is the Fuzzy Logic Toolbox For Use With MATLAB® program produced by the Math Works Inc., of Natwick, Mass. Once the threshold look up table 186 has been computed, the tissue/flow determination can be made in real time. The color amplitude threshold values for the example described above are given in Appendix A.

Figure 7A:
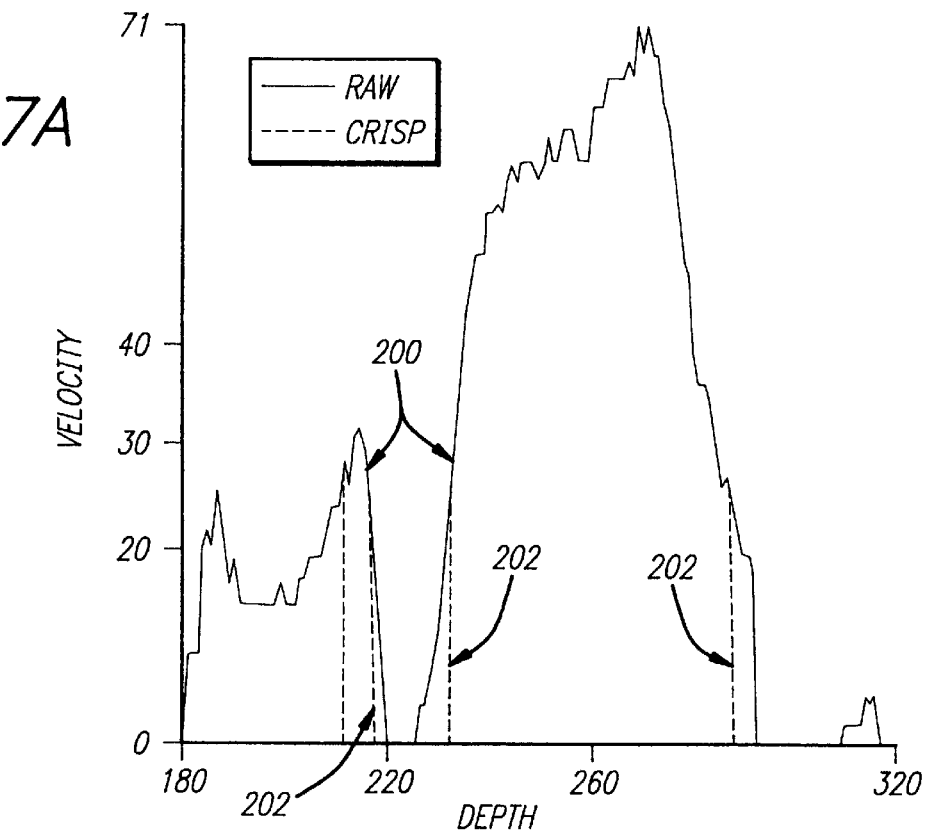
FIGS. 7A and 7B illustrate some experimental results that were obtained with a prior art, crisp tissue/flow determination system and the fuzzy logic tissue/flow determination system according to the present invention.
Figure 7B:
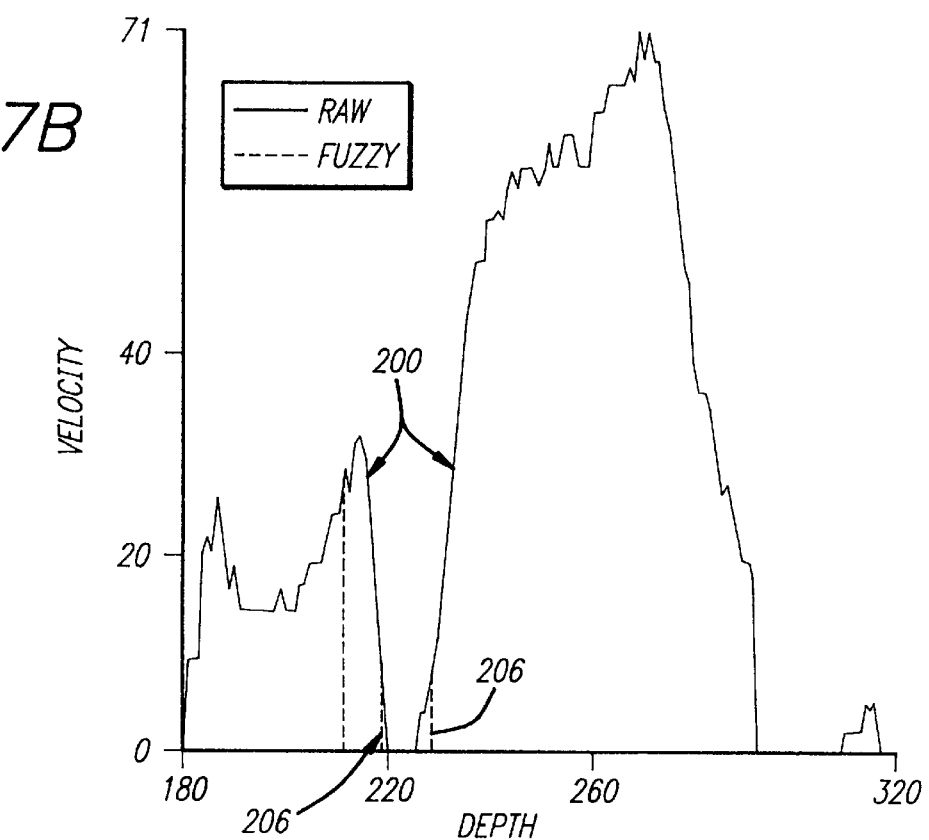

FIGS. 7A and 7B illustrate some experimental results that compare the fuzzy logic tissue/flow determination system according to the present invention with a prior art crisp, threshold tissue/flow determination system.

To perform the test, a single beam line of velocity data was obtained from a Siemens' Sonoline® Elegra ultrasound imaging system. The velocity data was plotted as a solid line on a graph that compares the velocity on the vertical axis with the depth of the tissue on the horizontal axis. A dotted line 202 plots the velocity values after being passed through a conventional tissue/flow determination system. As can be seen, at several points including the depth around 220 samples, a gap exists between the raw velocity data and the velocity determined from the crisp, threshold approach. The gap indicates that for the data shown in FIG. 7A, the conventional tissue/flow determination system was not able to detect blood flow below approximately 30 units out of 250.

In contrast, FIG. 7B illustrates the results obtained with the same set of velocity data shown in FIG. 7A, but analyzed by the fuzzy logic tissue/flow determination system according to the present invention. Again, the raw velocity data is plotted as a solid line 200 on a graph of the velocity on the vertical axis versus the depth of tissue on the horizontal axis. A dotted line 206 indicates the output of the fuzzy logic tissue/flow determination system according to the present invention. As can be seen, the gap between the dotted line 206 and the actual velocity data is smaller than the gaps that occur in FIG. 7A. Therefore, the tissue/flow determination system according to the present invention is able to detect lower flow rates for display in an ultrasound image.

As described above, the present invention is a tissue/flow determination system that can more intelligently and accurately determine the presence of flow conditions in ultrasonic signals that could be produced as a result of tissue movement, cardiac cycles, breathing, or transducer movement. Using the present invention, more accurate images of internal body matter of a patient can be obtained and presented to a physician or sonographer for diagnosis.

The embodiments of the invention in which an exclusive property or privilege is claimed are defined as follows:

1. A method of determining tissue/flow conditions from echo amplitude, color amplitude, and velocity ultrasound signals, comprising:

precomputing according to a set of fuzzy logic rules a number of color amplitude thresholds against which the color amplitude signal is compared to determine if the echo amplitude, color amplitude and velocity signals are to be displayed as flow or as tissue;

selecting from a memory one of the number of color amplitude thresholds based on a value of the echo amplitude and velocity signals, comparing the color amplitude signal with the selected color amplitude threshold; and displaying the echo amplitude, color amplitude, and velocity signals as flow if the color amplitude signal exceeds the selected color amplitude threshold or displaying the echo amplitude, color amplitude, and velocity signals as tissue if the color amplitude signal is less than the selected color amplitude threshold.

2. The method of claim 1, wherein the step of precomputing a number of color amplitude thresholds comprises:

applying the echo amplitude, color amplitude and velocity signals to the set of fuzzy rules that produce an indication of the plausibility that the echo amplitude, color amplitude, and velocity signals represent a tissue or flow condition; and analyzing the plausibility to select the color amplitude threshold for each possible echo amplitude and velocity value above which the echo amplitude, color amplitude, and velocity values represent a flow condition.

3. An ultrasound imaging system for creating color images of a patient, comprising:

a transducer for directing ultrasonic signals into the patient and receiving echo signals from the patient;

a beamformer that receives the echo signals and combines them;

a B-mode processor that receives the combined echo signals and produces a signal indicative of the amplitude of the combined echo signals;

a color mode processor that receives the combined echo signals and produces a color amplitude signal and a velocity signal that are indicative of the amplitude and velocity of a non-stationary part of the combined echo signals;

a tissue/flow processor that analyzes the signal indicative of the amplitude of the combined echo signals, and the color amplitude and velocity signals that are indicative of the non-stationary part of the combined echo signals to determine whether a source of the echo signals is tissue or moving blood flow, the tissue/flow processor including a memory that stores a number of color threshold values that indicates that the source of the echo signals is moving blood flow if the color amplitude signal exceeds a selected color threshold value that is determined by a value of amplitude and velocity signals;

a monitor that is directed by the tissue/flow processor to display the combined echo signals as greyscale pixels if the source of the echo signals is tissue or displays the combined echo signals as color pixels if the source of the echo signals is moving blood flow.

4. The ultrasound system of claim 3, further comprising a scan converter that receives the signals indicative of the amplitude of the combined echo signals and the signals indicative of the velocity of the combined echo signals, and wherein the output of the scan converter are the signals applied to the tissue/flow processor.

5. The ultrasound system of claim 3, wherein the memory only stores color threshold values that vary with changes in the amplitude and velocity signals.

6. The ultrasound system of claim 3, wherein the tissue/flow processor further comprises a look up table associated with the amplitude and velocity signals that scales the amplitude and velocity signals into a range where the color threshold values change.

* * * * *